US007327849B2

(12) United States Patent
Sommerfeldt et al.

(10) Patent No.: US 7,327,849 B2
(45) Date of Patent: Feb. 5, 2008

(54) ENERGY DENSITY CONTROL SYSTEM USING A TWO-DIMENSIONAL ENERGY DENSITY SENSOR

(75) Inventors: Scott David Sommerfeldt, Mapleton, UT (US); Benjamin Mahonri Faber, Spanish Fork, UT (US)

(73) Assignee: Brigham Young University, Provo, UT (US)

( * ) Notice: Subject to any disclaimer, the term of this patent is extended or adjusted under 35 U.S.C. 154(b) by 356 days.

(21) Appl. No.: 10/913,312

(22) Filed: Aug. 9, 2004

(65) Prior Publication Data

US 2006/0029233 A1 Feb. 9, 2006

(51) Int. Cl.
*A61F 11/06* (2006.01)

(52) U.S. Cl. .................. 381/71.7; 381/71.1; 381/71.2; 381/71.3; 381/71.4; 381/71.14; 381/71.5; 381/92

(58) Field of Classification Search .... 381/71.1-71.13, 381/86, 91, 92, 122
See application file for complete search history.

(56) References Cited

U.S. PATENT DOCUMENTS 5,602,926 A * 2/1997 Ohashi et al. ............ 381/71.5
5,689,572 A * 11/1997 Ohki et al. ............... 381/71.3
5,699,437 A * 12/1997 Finn ......................... 381/71.7
5,724,432 A 3/1998 Bouvet et al.
6,192,133 B1 * 2/2001 Enamito et al. ........... 381/71.5
6,600,824 B1 * 7/2003 Matsuo ....................... 381/92
6,694,028 B1 * 2/2004 Matsuo ....................... 381/92
6,760,449 B1 * 7/2004 Matsuo ....................... 381/92
7,031,474 B1 * 4/2006 Yuen et al. ..................... 381/1
2003/0053635 A1 * 3/2003 Carme et al. .............. 381/71.5
2003/0219132 A1 11/2003 Summerfeldt et al.
2004/0105557 A1 * 6/2004 Matsuo ....................... 381/92
2004/0247137 A1 * 12/2004 Inoue et al. ............... 381/71.4
2005/0084115 A1 * 4/2005 Enamito et al. ........... 381/71.7

FOREIGN PATENT DOCUMENTS

EP 0 568 282 A3 3/1993

OTHER PUBLICATIONS

T.C. Yang and C. H. Tseng , "integrating and Automating Analysis And Optimization" Jul. 4, 1992 , Computers & structures vol. 48, No. 6,pp. 1083-1106.*
UK Search Report Under Section 17—Patents Act 1977, Date of Search: Oct. 17, 2005.

(Continued)

*Primary Examiner*—Vivian Chin
*Assistant Examiner*—Disler Paul
(74) *Attorney, Agent, or Firm*—Finnegan, Henderson, Farabow, Garrett & Dunner

(57) ABSTRACT

A system and method of reducing noise in an enclosure is disclosed. The method includes receiving at least one reference signal; receiving pressure signals from no more than two substantially orthogonally placed pairs of acoustic sensors, where one pair of acoustic sensors is in the x-direction and one pair of acoustic sensors is in the y-direction, and where the acoustic sensors are placed in a plane which is substantially parallel and in proximity to an inner surface of the enclosure; using the pressure signals and the reference signal to generate an output signal to minimize energy density at a location of the acoustic sensors; and sending the output signal to an acoustic actuator.

35 Claims, 5 Drawing Sheets

OTHER PUBLICATIONS

*Real Time Control of Sound Pressure And Energy Density In A Mining Vehicle Cabin*, C.H. Hansen, D.A. Stanef and R.C. Morgans—(Dept. of Mechanical Engineering, Univ. of Adelaide, Australia); Tenth International Congress on Sound and Vibration Jul. 7-10, 2003 Stockholm, Sweden; pp. 3713-3719.

*Active Minimization Of Acoustic Energy Density In Enclosed Sound Fields*, Benjamin M. Faber, A thesis submitted to the faculty of Brigham Young University in partial fulfillment of the requirements for the degree of Master of Science; Department of Physics and Astronomy, Brigham Young University 2004.

* cited by examiner

ENERGY DENSITY CONTROL SYSTEM USING A TWO-DIMENSIONAL ENERGY DENSITY SENSOR

TECHNICAL FIELD

The method and system disclosed relate to the field of acoustic noise reduction, and more specifically, a system for and method of using one or more two-dimensional energy density sensors feeding a control system to effectively diminish acoustic noise.

BACKGROUND

Over the years, many attempts have been made to eliminate unwanted or harmful sounds, i.e., noise. The most used technique is passive noise cancellation, which attempts to eliminate noise by muffling the noise with dampers. Passive noise control is often performed with insulation, ceiling tiles, and mufflers. Unfortunately, passive noise control systems can be bulky and work best on middle and high frequency sounds.

An attractive alternative to passive noise cancellation is active noise cancellation ("ANC"). Active noise cancellation is sound field modification by electro-acoustical means, generally by generating acoustical signals that are out of phase with the noise. In essence, active noise cancellation systems attempt to generate, electronically, a sound field that is the mirror image of the noise to be cancelled. Research into active noise cancellation began in the 1930's, with the earliest patent on active noise cancellation being granted to Lueg (U.S. Pat. No. 2,043,416) in 1936. Research continued into the 1950's with Olson and May developing an electronic sound absorber that provided a feedback mechanism for attenuating low frequency noise near a microphone. H. F. Olsen and E. G. May, "Electronic Sound Absorber," *J. Acoust. Soc. Am.* 25, 1130-1136 (1953). Unfortunately, the Olson and May electronic sound absorber was unstable at higher frequencies.

Within the last 30 years, digital signal processing and advances in control theory have fed increased interest and research into active noise cancellation. This research has brought to market commercially viable active noise cancellation systems. Active noise cancellation systems are found in higher-end headphones, vehicles, and HVAC systems.

Vehicles provide a convenient example of the current use of active noise cancellation in enclosed spaces. In order to achieve active noise cancellation in vehicles, error sensors, i.e., acoustic sensors or microphones, are often placed in close proximity to the operator's head in order to detect the three-dimensional sound waves, or noise, to which the operator of the vehicle is subjected. Unfortunately, acoustic sensors located in this manner often interfere with the operator's vision, flexibility, and comfort. In addition, such acoustic sensor placement tends to provide only localized control, rather than global control of unwanted noise.

Most active noise cancellation systems focus on reducing noise by minimizing the squared acoustic pressure ("SP"). However, research by Sommerfeldt at Penn State University showed that minimizing acoustic energy density ("ED") has advantages over minimizing SP. Acoustic energy density looks at both the pressure of the acoustic wave and its velocity. J. W. Parkins, S. D. Sommerfeldt, and J. Tichy, "Narrowband and Broadband Active Control in an Enclosure Using the Acoustic Energy Density," *J. Acoust. Soc. Am.* 108, 192-203 (2000). Control of ED also has the benefit over SP in that there is less sensitivity to error sensor placement within an enclosed sound field. Using SP techniques in an enclosed sound field, there are nodal planes that exist in the three orthogonal directions; whereas, using ED, there are merely nodal lines that exist at the intersection of two orthogonal nodal planes of pressure. Therefore, for a given placement of the sensor, there is a much higher probability of the sensor being placed away from nodes. Also, ED provides more global attenuation of the noise than SP.

ED depends on acoustic particle velocity, as well as acoustic pressure. Because particle velocity is a three-dimensional quantity, most existing ED ANC systems utilize a three-dimensional energy density sensor having six acoustic sensors, with two in each of the three orthogonal directions. Each pair of acoustic sensors provides signals to a control system to yield the particle velocity component in the orthogonal direction of the pair. The vector sum of the three velocity components from the three pairs of orthogonal acoustic sensors yields particle velocity. An average of the six acoustic sensors yields acoustic pressure. A drawback of existing ED ANC systems is the additional computing power required to perform the calculations with the three-dimensional inputs forming the error signal. While certain research organizations have utilized a four-microphone ED sensor, the four microphones are arranged in a tetrahedron configuration and are used for conventional three-dimensional sensing in an SP system.

The present invention is directed to overcoming the one or more problems or disadvantages associated with the prior art.

SUMMARY OF THE INVENTION

In accordance with a disclosed embodiment, a method of reducing noise in an enclosure is described. The method includes receiving at least one reference signal; receiving pressure signals from no more than two substantially orthogonally placed pairs of acoustic sensors, where one pair of acoustic sensors is in the x-direction and one pair of acoustic sensors is in the y-direction, and where the acoustic sensors are placed in a plane which is substantially parallel and in proximity to an inner surface of the enclosure; using the pressure signals and the reference signal to generate an output signal to minimize energy density at a location of the acoustic sensors; and sending the output signal to an acoustic actuator.

In accordance with another aspect of the disclosed embodiment, a machine-readable storage medium is described. The storage medium has stored thereon machine executable instructions. The execution of the instructions is adapted to implement a method of reducing noise in an enclosure. The method comprising: receiving at least one reference signal; receiving pressure signals from no more than two substantially orthogonally placed pairs of acoustic sensors, where one pair of acoustic sensors is in the x-direction and one pair of acoustic sensors is in the y-direction, and where the acoustic sensors are placed in a plane which is substantially parallel and in proximity to an inner surface of the enclosure; using the pressure signals and the reference signal to generate an output signal to minimize energy density at a location of the acoustic sensors; and sending the output signal to an acoustic actuator.

In accordance with another aspect of the disclosed embodiment, a system for reducing noise in an enclosure is described. The system includes a reference signal; an acoustic actuator; a sensor device including no more than two substantially orthogonally placed pairs of acoustic sensors, where one pair of acoustic sensors is in the x-direction and one pair of acoustic sensors is in the y-direction, and where the acoustic sensors are placed in a plane which is substantially parallel and in proximity to an inner surface of the enclosure; and a controller in communication with the reference signal, the acoustic actuator, and the sensor. The controller is operable to: receive the reference signal; receive pressure signals from the sensor device; use the pressure signals and the reference signal to generate an output signal to minimize energy density at a location of the sensor device; and send the output signal to the acoustic actuator.

The foregoing summarizes only a few aspects of the disclosed embodiment and is not intended to be reflective of the full scope of the embodiments claimed. Additional features and advantages are set forth in the following description, may be apparent from the description, or may be learned by practicing the teachings of the disclosure. Moreover, both the foregoing summary and the following detailed description are exemplary and explanatory and are intended to provide further explanation of what is claimed.

BRIEF DESCRIPTION OF THE DRAWINGS

The accompanying drawings, which are incorporated in and constitute a part of this specification, illustrate one embodiment and together with the description, serve to explain the principles of the operation of the embodiment.

DETAILED DESCRIPTION

Figure 1:
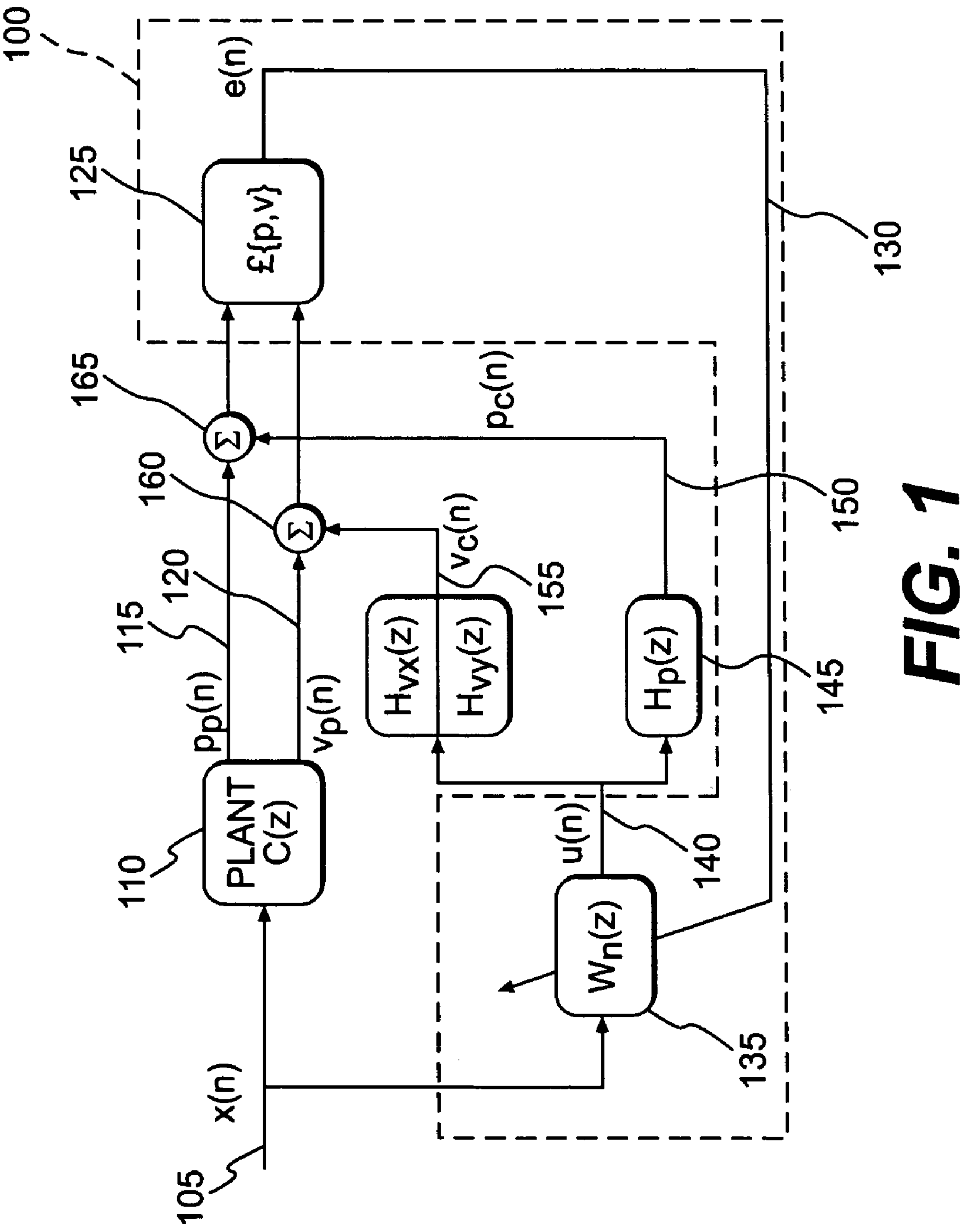
FIG. 1 illustrates a block diagram of a modified filtered-x LMS control system.

Reference will now be made in detail to the present exemplary embodiments, examples of which are illustrated in the accompanying drawings. Wherever possible, the same reference numbers will be used throughout the drawings to refer to the same or like parts.

Unlike energy density active noise cancellation systems that use a three-dimensional sensor to sense the energy density and provide the raw inputs for an error signal to a control system, the present system utilizes a two-dimensional sensor to provide an error signal to the control system. By mounting the two-dimensional sensor on or relatively close to a rigid surface within an enclosed space, such as a vehicle cabin, and orienting the acoustic sensors in a plane that is parallel to the rigid surface, the velocity component of the particle velocity in the direction normal to the rigid surface is known, i.e., zero. Thus, the inventors have discovered that a two-dimensional sensor may be used in place of a three-dimensional sensor, significantly reducing the number of required computations, acoustic sensors, associated hardware, and computing power of the ANC system. In addition, the size and shape of a two-dimensional sensor is significantly smaller and planer than a three-dimensional system, thus permitting more discrete placement of the sensor within the enclosed space.

In one cylindrical embodiment where the sensors are mounted in a cylinder, the aspect ratio of the cylindrical, two-dimensional sensor is 2/5, where the aspect ratio is the depth of the cylinder divided by the diameter of the cylinder. For this aspect ratio, the effective acoustic separation distance of the acoustic sensors is 3/2 the physical separation distance.

An enclosure need not be limited to a space completely enclosed by walls, for example a cubic area enclosed by six surfaces. Instead, as used in the present description, an enclosure may comprise any space having at least two opposed surfaces or walls. The walls need not be in close proximity to each other. For example, one wall of an enclosure may be formed by an outside surface of a machine inside of a factory with the other wall formed by an inside wall of the factory.

The total energy in an acoustic field is composed of both potential and kinetic energy quantities. The potential energy is a function of acoustic pressure, and the kinetic energy is a function of the acoustic particle velocity.

The potential energy may be expressed by:

$$E_p = \frac{1}{2}\left(\frac{p^2}{\rho_0 c^2}\right)V_0,$$

where p is acoustic energy, $\rho_0$ is the ambient density of air, c is the speed of sound, and $V_0$ is the volume of air containing the potential energy. The total kinetic energy in a volume of air may be expressed by:

$$E_k = \frac{1}{2}\rho_0 V_0 u^2,$$

where u is the magnitude of the acoustic particle velocity. The instantaneous total acoustic energy density is the sum of the potential energy density and the kinetic energy density and may be expressed by:

$$E_i = \frac{1}{2}\rho_0\left[u^2 + \left(\frac{p}{\rho_0 c}\right)^2\right].$$

By assuming the density of air and the speed of sound in air to be known constants, only the acoustic pressure and the particle velocity need be measured in order to calculate ED. Using a pair of acoustic sensors, particle velocity can be measured along the axis of the acoustic sensors in a single direction. Two orthogonal pairs of acoustic sensors placed parallel and in close proximity to a surface yields particle velocity along three axes: along the x and y axes defined by the two pairs of orthogonally placed acoustic sensors, and a known measure of zero velocity normal to the acoustic sensors and the rigid surface. Therefore, a two dimensional sensor coupled to a control system and one or more acoustic actuators may form an effective ANC system.

Control systems consistent with the disclosed embodiment may utilize a feedforward control system. Feedforward control systems accept a reference input to predict incoming noise in advance, so that a suitable control signal can be generated in enough time to counteract the noise. If one considers vibration of the walls of the enclosed space as the noise source, the present system uses the principle of superposition of acoustic waves to alter the acoustic radiation impedance seen by the noise source, such that the acoustical energy radiated by the noise source is minimized.

A filtered-x LMS algorithm, well known to those skilled in the art, may be modified for implementation of the disclosed control system. The standard filtered-x LMS algorithm is intended for use with SP systems. A modified filtered-x LMS algorithm takes into account that its use is for an ED system that depends on both acoustic pressure and acoustic particle velocity.

FIG. 1 illustrates a block diagram of a modified filtered-x LMS control system 100. A reference signal, x(n), 105 is fed into the system. Reference signal 105 may be, for example, a tachometer signal from a noise source such as a vehicle engine. The reference signal 105 enters plant 110, for example an engine enclosure or cabin, and produces noise, which in terms of energy density control comprises sound pressure 115 and sound particle velocity 120. An enclosure is a space having at least two substantially opposed sides. Sound particle velocity is a three-dimensional vector quantity and all three components may potentially contribute to the energy density.

Control system 100 receives reference signal 105 and applies a finite impulse response ("FIR") filter 135 to the reference signal to produce an output signal, u(n), 140. Output signal 140 travels through a secondary path, H(z), 145 through which output signal 140 must travel before returning into control system 100 as a contribution to the error signal, e(n), 130. Secondary path 145 may comprise effects inherent in hardware implementations of control system 100, e.g., effects from digital-to-analog converters, filters, audio power amplifiers, acoustic actuators, acoustical transmission path, error sensors, signal conditioning electronics, antialiasing filters, and analog-to-digital converters. The output of secondary path 145 comprises cancellation pressure 150 and cancellation particle velocity 155. Superposition of these sound waves, illustrated by velocity summation symbol 160 and pressure summation symbol 165, should reduce the noise. Processing block 125 senses the actual, reduced noise level of the enclosed space, and computes an actual gradient of the energy density quantity from pressure and velocity components in the orthogonal x and y directions. Processing block 125 sends the energy density gradient quantity as an error signal to FIR filter 135.

FIR filter 135 incorporates secondary path effects in its control filter coefficients. An estimate of the secondary path effects may be obtained through a process of system identification. System identification models the transfer functions of the secondary paths 145. System identification may be performed online while the system is running or offline. Offline system identification may be performed by injecting a known signal into the unknown system and measuring the output of the system. An example of a known signal is white noise. Performance of system identification will establish the coefficients for FIR filters 145.

Figure 2:
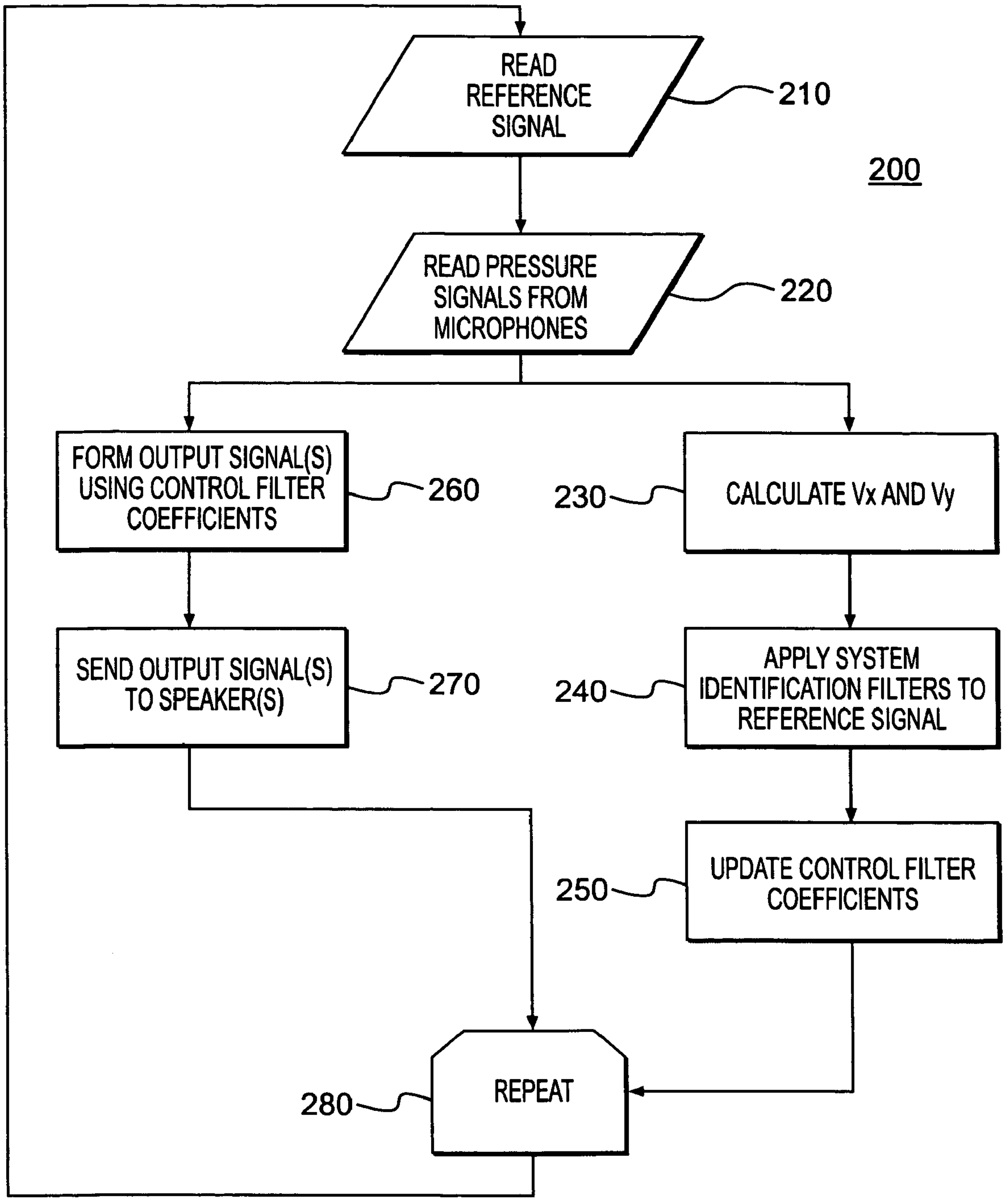
FIG. 2 is a flow chart illustrating the operation of the control system for reducing the noise in an enclosure.

FIG. 2 is a flow chart illustrating the operation of the control system 100 for reducing the noise in an enclosure. Control system 100 receives reference signal 105 of the dominant tonal component of the noise to be reduced (stage 210). In addition to reference signal 105, control system 100 receives pressure signals from two orthogonal pairs of acoustic sensors placed parallel and in close proximity to a surface inside the enclosure (stage 220). By placing the acoustic sensors in close proximity to a surface in the enclosure, velocity normal to the surface becomes a known quantity, zero, and additional acoustic sensors and processing power are not required.

Control system 100 calculates the noise particle velocity in the x and y direction according to the following equation:

$$v = \frac{1}{\rho}\int\frac{(p_2 - p_1)}{\Delta x}dt$$

where ρ is the density of the air, Δx is the effective distance between the acoustic sensors in a pair, and p is the noise pressure at each acoustic sensor of the pair. The equation is calculated to generate a $V_x$ and a $V_y$. In addition, the average noise pressure is calculated, for example, by averaging the pressure sensed at the four acoustic sensors (stage 230). Those skilled in the art will appreciate that three acoustic sensors may be used in place of two pairs of orthogonally placed acoustic sensors because three points suffice to define a plane. Thus, the calculations would change appropriately for a three-acoustic sensor system as layout and trigonometry of the acoustic sensor configuration would dictate.

Each cycle of a controller in control system 100 may update the FIR filter's control filter coefficients. This is a two step process: system identification filters generated in a system identification process may be applied to the reference signal to produce filtered-x signals (stage 240); and, the filtered-x signals in conjunction with error signal 130 are used to update the value of the control filter coefficients, $w_i(n)$ (stage 250).

Returning to stage 240, in a system having two output acoustic actuators, six filtered-x signals are formed: pressure for the first acoustic actuator, $r_{p,1}(n)$; velocity in the x direction for the first acoustic actuator, $r_{vx,1}(n)$; velocity in the y direction for the first acoustic actuator, $r_{vy,1}(n)$; pressure for the second acoustic actuator, $r_{p,2}(n)$; velocity in the x direction for the second acoustic actuator, $r_{vx,2}(n)$; and velocity in the y direction for the second acoustic actuator, $r_{vy,2}(n)$. The form of the filtered-x signals is, for example for the x direction for the first acoustic actuator:

$$r_{vx,1}(n) = \sum_{j=0}^{J-1}\hat{h}_{vx,1}(j)x(n-j)$$

where the ĥ coefficients are the system identification coefficients obtained from the system identification process (stage 240). The larger the value of J, the greater the number of system identification coefficients that are determined. The ĥ coefficients in essence model the impulse response from the control output to the sensor input, or, as previously described models the secondary path 145. Increasing the number of system identification coefficients increases the portion of the impulse response that can be modeled. Increasing the number of system identification coefficients beyond the number necessary to capture most of the energy in the impulse response yields diminishing returns.

The control filter coefficients may be updated during each cycle of the controller (stage 250). Each output, one for each acoustic actuator, has an associated FIR filter 135. Control filter coefficients are updated using the filtered-x signals and reference signal 105, according to the following formula:

$$w_i(n+1) = w_i(n) - \mu\rho c v_x(n) r_{vx}(n-i) - \mu\rho c v_y(n) r_{vy}(n-i) - \mu p(n) r_p(n-i)$$

where i is from 0 to I−1 (where I may typically range from 8 to 128), c is the speed of sound, and μ is the filter convergence factor (typically around $10^{-9}$ to $10^{-12}$). As can be seen from the above equation, the control filter coefficients use both the current and past filtered-x signals, so the controller may maintain a buffer of current past values of these signals in memory. The rate at which the filter converges is controlled by μ. A large value of μ increases filter convergence speed, but increasing the value too far may reduce the amount of attenuation achieved and may eventually make the control system become unstable.

While the control system is calculating updates to FIR filter 135 for use during the next control cycle (in stages 230-250), the control system applies current control filter coefficients to the reference signal to acoustically cancel the noise (stages 260 and 270). The controller generates two output signals 140, one for each control channel, using current estimates of the control filter coefficients (stage 260) according to the following equation:

$$u(n) = \sum_{i=0}^{I-1} w_i(n)x(n-i)$$

where I represents the number of filter coefficients and $w_i$ are the filter coefficients. Generally, 32 or less coefficients suffice to provide good control of the system.

The control system takes the one or more output signals and drives a respective acoustic actuator (stage 270). The controller then returns to read the reference signal (stage 210) and repeat the process (stage 280).

INDUSTRIAL APPLICABILITY

Figure 3:
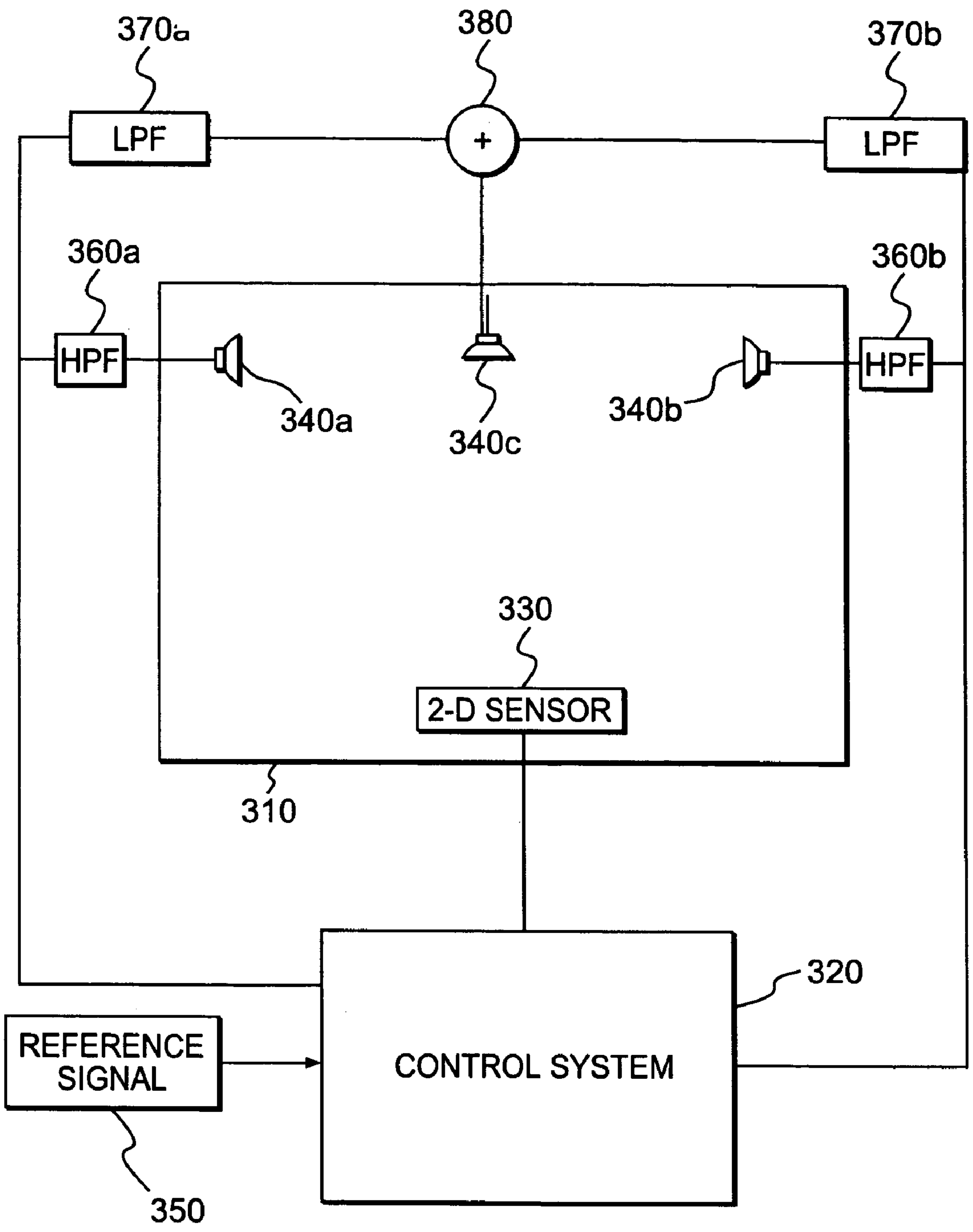
FIG. 3 illustrates an implementation of an energy density ANC control system using a two-dimensional sensor.

FIG. 3 illustrates an implementation of an energy density ANC control system using a two-dimensional sensor 330. The ANC control system uses two-dimensional sensor 330 to sense particle velocity in two orthogonal directions and measure acoustic pressure in an enclosed space, such as vehicle cabin 310. Two-dimensional sensor 330 is placed normal to and in proximity to a surface inside of the vehicle cabin. Sensor 330 may be placed hidden from sight, for example under the headliner of vehicle cabin 310. Signals from two pairs of acoustic sensors that form two-dimensional sensor 330 are in communication with a control system 320. Control system 320 may include a digital signal processor, for example a Texas Instruments DSP or a Motorola DSP, or a microprocessor. Control system 320 operates in accordance with the operations described with reference to FIGS. 1 and 2.

Control system 320 may also include an input/output board for communication with two-dimensional sensor 330 and signal conditioning electronics. The input/output board utilized in control system 320 may include, for example, 12 bit digital-to-analog converters ("DAC") and analog-to-digital ("ADC") converters. The signal conditioning electronics may provide for an adjustable gain on the inputs from two-dimensional sensor 330. For example, gains of 0, 10, or 20 dB may be applied and fine-tuned for each acoustic sensor in two-dimensional sensor 330. In addition, the analog signals from sensor 330 may be low-pass filtered before the ADC's to reduce aliasing and digital signals from the DSP may be filtered after the DAC's to eliminate any undesired high frequency content due to quantization.

Control system 320 uses the input from two-dimensional sensor 330 as the energy density error signal. A reference signal 350 is fed into control system 320, for example, from an engine tachometer. Reference signal 350 may be low pass filtered.

Noise in vehicles may be dominated by tonal components that are related to the rotation speed of rotating components such as the engine. For example, in a typical six-cylinder engine, the engine firing frequency is three times that of the engine rotation frequency and is generally the dominant tonal component of the noise inside the cabin of the vehicle. Engine firing frequency typically ranges from 40 Hz to 200 Hz. Thus, reference signal 350 may correspond to the engine firing frequency.

The outputs of control system 320 may be fed to one or more acoustic actuators 340*a-c*. In a typical installation, acoustic actuators 340*a* and 340*b* represent left and right acoustic actuators and receive their respective control signals through a respective high pass filter. Acoustic actuator 340*c* may be a subwoofer and receive both the left and right outputs of control system 320 through a pair of low pass filters through a summer 380. Thus, subwoofer 340*c* serves to produce output frequencies for both output channels of control system 320. Subwoofer 340*c* is not required to be used with system 300, but does provide additional assistance in the low frequency ranges. Acoustic actuators 340 may be part of the standard entertainment system installed in the vehicle, with the signals from control system 320 being mixed into the sound output of the entertainment systems output amplifier. Or, control system 320 may be integrated into the standard entertainment system of the vehicle and share the output amplifiers of the standard entertainment system.

While the above implementation is discussed with reference to a single two-dimensional sensor, multiple sensors may be used. In addition, greater or fewer output channels than two may also be utilized.

Figure 4:
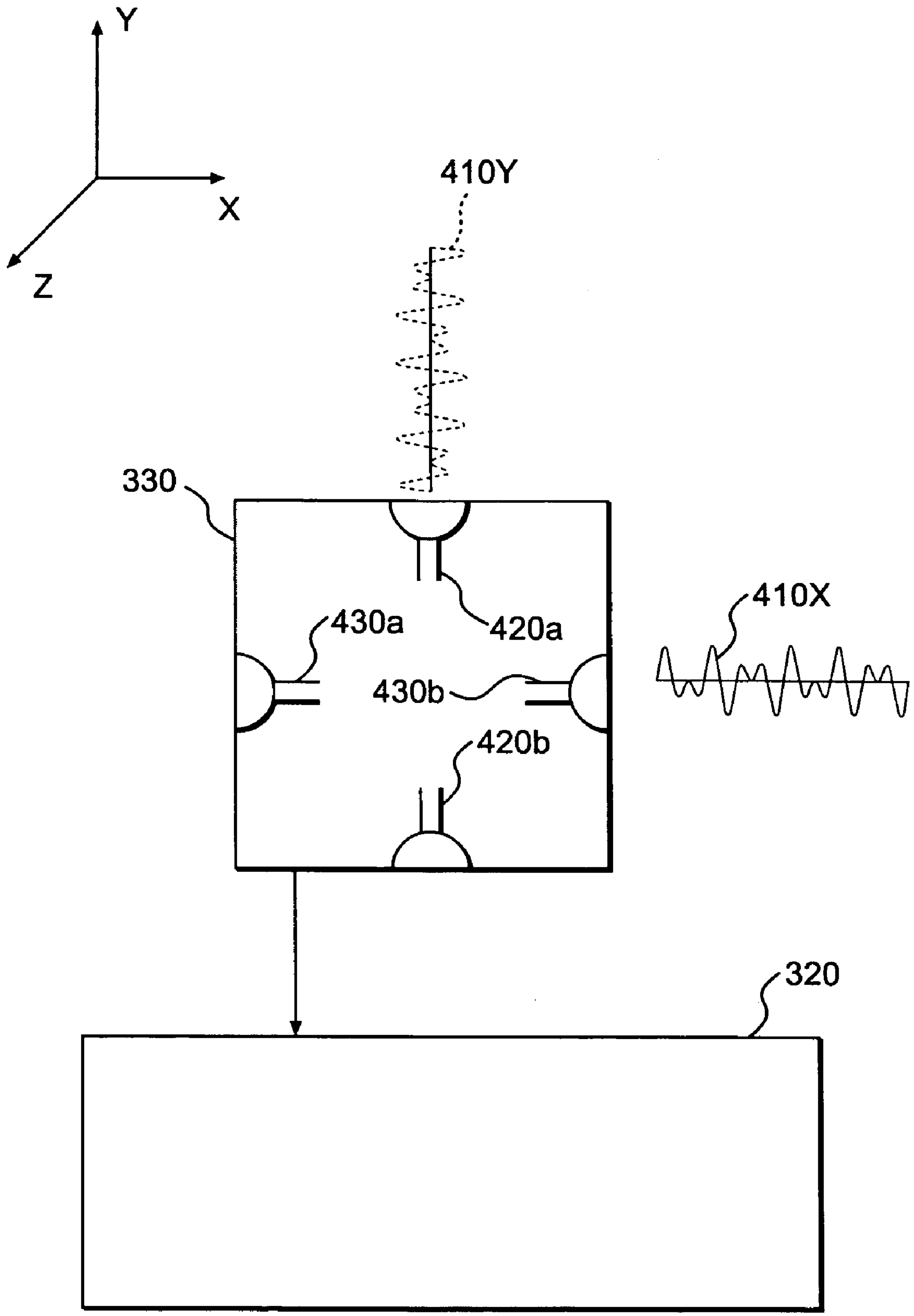
FIG. 4 illustrates the two-dimensional sensor.

FIG. 4 illustrates the two-dimensional sensor 330 . Two-dimensional sensor 330 comprises two pairs of acoustic sensors 420 and 430 aligned orthogonally. The distance between the acoustic sensor pairs is known and may be used in the velocity equations previously described. Each acoustic sensor in acoustic sensor pair 420, 430 receives an acoustic pressure from the environment for passing to control system 320 for calculation of particle velocity and average acoustic pressure. For example, acoustic sensor pair 430 receives pressure from sound wave 410*x*, and acoustic sensor pair 420 receives pressure from sound wave 410*y*. As previously mentioned, those skilled in the art will appreciate that with appropriate changes in control system 320, a three-acoustic sensor system could be used.

Figure 5:
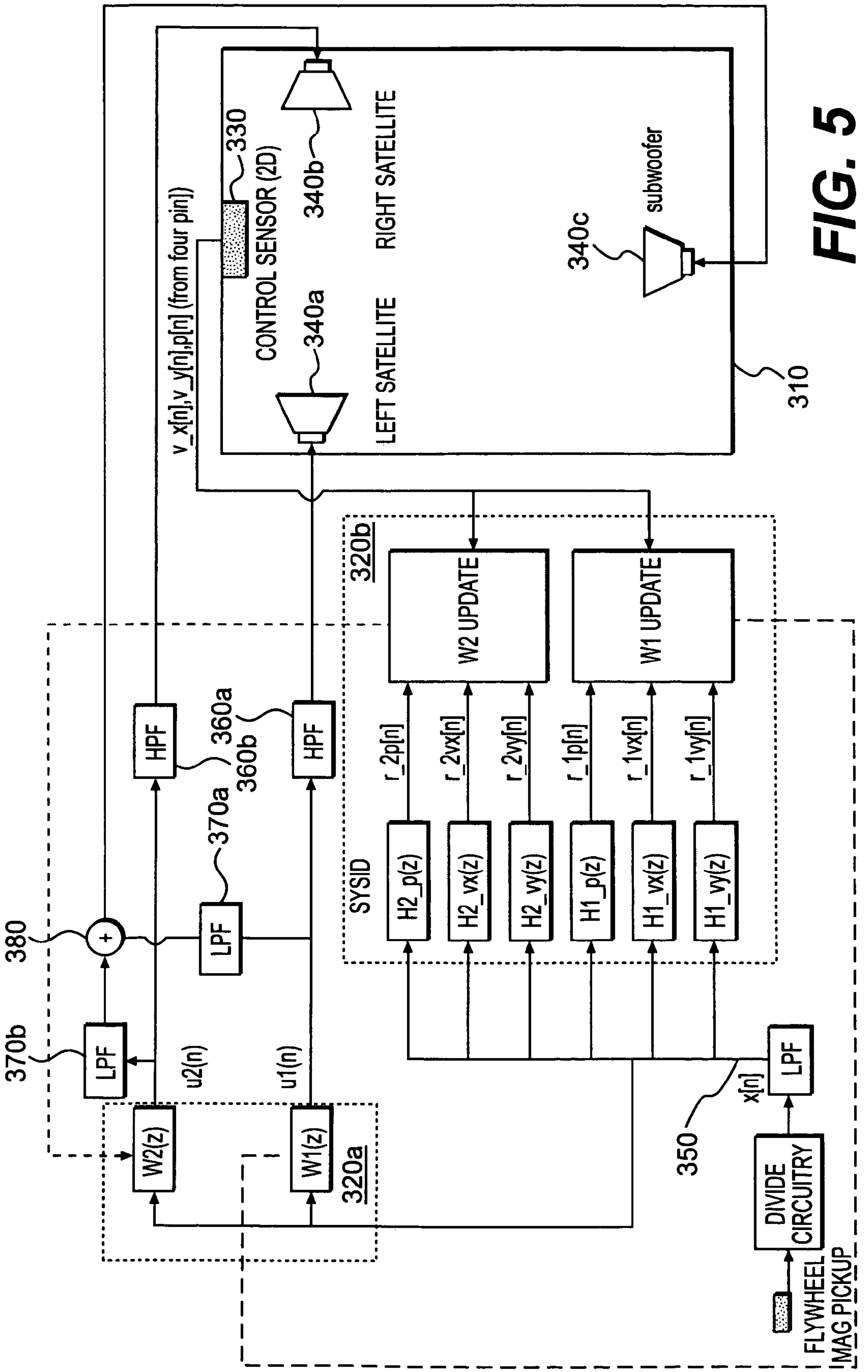
FIG. 5 illustrates further details of a control system.

FIG. 5 illustrates further details of control system 320. In particular, control system 320 includes a control coefficient updating process 320*b*. The control coefficient updating process uses system identification filters applied to the reference signal to produce a filtered-x signal. The filtered-x signal in conjunction with the error signal from control sensor 330 is used to update the value of control filter coefficients $w_i(n)$. These functions were previously described with reference to Stages 240 and 250 of FIG. 2. Coefficient updating process 320*b* illustrates functional elements for a two-channel system. The control coefficients generated from the coefficient updating process are utilized in FIR filter 320*a* to generate output signals for the two channels as previously described with respect to stage 260 of FIG. 2.

In addition, aspects of the present system may be utilized, for example, to reduce noise in proximity to a machine on a factory floor. The sensor 330 may be placed normal to and in proximity of a surface of the machine. The surface of the machine may be proximate to the location of a machine operator, such that noise around the operator will be reduced. The enclosure includes the space proximate to the machine formed by the surface of the machine and an additional surface, such as an interior wall of the factor, another machine surface, or the surface of a dividing wall.

It will be readily apparent to those skilled in this art that various changes and modifications of an obvious nature may be made, and all such changes and modifications are considered to fall within the scope of the appended claims. Other embodiments will be apparent to those skilled in the art from consideration of the specification and practice of the disclosure. It is intended that the specification and examples be considered as exemplary only, with a true scope and spirit of the disclosure being indicated by the following claims and their equivalents.

What is claimed is:

1. A method of reducing noise in an enclosure, comprising:

receiving at least one reference signal;

receiving pressure signals from no more than two substantially orthogonally placed pairs of acoustic sensors, where one of said pairs of acoustic sensors is in the x-direction and the other of said pairs of acoustic sensors is in the y-direction, and where the acoustic sensors are placed in a plane which is substantially parallel to and in proximity to an inner surface of the enclosure such that the velocity component of a particle velocity in the direction normal to the inner surface becomes a predetermined constant;

using the pressure signals and the reference signal to generate an output signal to minimize energy density at a location of the acoustic sensors; and sending the output signal to an acoustic actuator.

2. The method of claim 1, wherein using the pressure signals further includes generating an x-direction velocity signal from the pressure signals from the pair of acoustic sensors in the x-direction and a y-direction velocity signal from the pressure signals from the pair of acoustic sensors in the y-direction.

3. The method of claim 2, further including generating an average pressure signal from one or more of the received pressure signals.

4. The method of claim 1, further including applying control filter coefficients to the reference signal to generate the output signal.

5. The method of claim 2, further including applying system identification filters to the reference signal to generate filtered-x signals.

6. The method of claim 5, further including applying the filtered-x signals to the x-direction velocity signal, the y-direction velocity signal, and the average pressure signal to update the control filter coefficients.

7. The method of claim 4, wherein applying control filter coefficients further includes applying control filter coefficients to generate a first output signal and a second output signal.

8. The method of claim 7, wherein sending the output signal to the acoustic actuator further includes sending the first output signal to a first acoustic actuator and the second output signal to a second acoustic actuator.

9. The method of claim 8, further including:

passing the first output signal through a low pass filter to a summer;

passing the second output signal through a low pass filter to the summer; and passing the output of the summer to at least one low frequency acoustic actuator.

10. The method of claim 8, further including passing the first output signal through a high pass filter prior to sending the first output signal to the first acoustic actuator.

11. The method of claim 1, further including mixing the output signal into a first output signal of a vehicle entertainment system.

12. A computer-readable storage medium having stored thereon machine executable instructions, the execution of said instructions adapted to implement a method of reducing noise in an enclosure, the method comprising:

receiving at least one reference signal;

receiving pressure signals from no more than two substantially orthogonally placed pairs of acoustic sensors, where one of said pairs of acoustic sensors is in the x-direction and the other of said pairs of acoustic sensors is in the y-direction, and where the acoustic sensors are placed in a plane which is substantially parallel to and in proximity to an inner surface of the enclosure such that the velocity component of a particle velocity in the direction normal to the inner surface becomes a predetermined constant;

using the pressure signals and the reference signal to generate an output signal to minimize energy density at a location of the acoustic sensors; and sending the output signal to an acoustic actuator.

13. The computer-readable storage medium of claim 12, wherein using the pressure signals further includes generating an x-direction velocity signal from the pressure signals from the pair of acoustic sensors in the x-direction and a y-direction velocity signal from the pressure signals from the pair of acoustic sensors in the y-direction.

14. The computer-readable storage medium of claim 13, further including generating an average pressure signal from one or more of the received pressure signals.

15. The computer-readable storage medium of claim 12, further including applying control filter coefficients to the reference signal to generate the output signal.

16. The computer-readable storage medium of claim 13, further including applying system identification filters to the reference signal to generate filtered-x signals.

17. The computer-readable storage medium of claim 16, further including applying the filtered-x signals to the x-direction velocity signal, the y-direction velocity signal, and the average pressure signal to update the control filter coefficients.

18. The computer-readable storage medium of claim 15, wherein applying control filter coefficients further includes applying control filter coefficients to generate a first output signal and a second output signal.

19. The computer-readable storage medium of claim 18, wherein sending the output signal to the acoustic actuator further includes sending the first output signal to a first acoustic actuator and the second output signal to a second acoustic actuator.

20. The computer-readable storage medium of claim 19, further including:

passing the first output signal through a low pass filter to a summer;

passing the second output signal through a low pass filter to the summer; and passing the output of the summer to at least one low frequency acoustic actuator.

21. The computer-readable storage medium of claim 19, further including passing the first output signal through a high pass filter prior to sending the first output signal to the first acoustic actuator.

22. The computer-readable storage medium of claim 12, further including mixing the output signal into a first output signal of a vehicle entertainment system.

23. A system for reducing noise in an enclosure, comprising:

an acoustic actuator;

a sensor device including no more than two substantially orthogonally placed pairs of acoustic sensors, where one of said pairs of acoustic sensors is in the x-direction and the other of said pairs of acoustic sensors is in the y-direction, and where the acoustic sensors are placed in a plane which is substantially parallel to and in proximity to an inner surface of the enclosure such that the velocity component of a particle velocity in the direction normal to the inner surface becomes a predetermined constant;

a controller in communication with the acoustic actuator and the sensor device, the controller operable to:

receive a reference signal;

receive pressure signals from the sensor device;

use the pressure signals and the reference signal to generate an output signal to minimize energy density at a location of the sensor device; and send the output signal to the acoustic actuator.

24. The system of claim 23, wherein the controller is further operable to generate an x-direction velocity signal from the pressure signals from the pair of acoustic sensors in the x-direction and a y-direction velocity signal from the pressure signals from the pair of acoustic sensors in the y-direction.

25. The system of claim 24, wherein the controller is further operable to generate an average pressure signal from one or more of the received pressure signals.

26. The system of claim 23, wherein the controller is further operable to apply control filter coefficients to the reference signal to generate the output signal.

27. The system of claim 24, wherein the controller is further operable to apply system identification filters to the reference signal to generate filtered-x signals.

28. The system of claim 27, wherein the controller is further operable to apply the filtered-x signals to the x-direction velocity signal, the y-direction velocity signal, and the average pressure signal to update the control filter coefficients.

29. The system of claim 26, wherein the controller is further operable to apply control filter coefficients to generate a first output signal and a second output signal.

30. The system of claim 29, wherein the controller is further operable to send the first output signal to a first acoustic actuator and the second output signal to a second acoustic actuator.

31. The system of claim 30, wherein the controller is further operable to:

pass the first output signal through a low pass filter to a summer;

pass the second output signal through a low pass filter to the summer; and pass the output of the summer to at least one low frequency acoustic actuator.

32. The system of claim 30, wherein the controller is further operable to pass the first output signal through a high pass filter prior to sending the first output signal to the first acoustic actuator.

33. The method of claim 1, wherein the predetermined constant is equal to zero.

34. The computer-readable storage medium of claim 12, wherein the predetermined constant is equal to zero.

35. The system of claim 23, wherein the predetermined constant is equal to zero.

* * * * *